United States Patent
Rightnour et al.

(10) Patent No.: US 7,316,730 B2
(45) Date of Patent: Jan. 8, 2008

(54) INLET DOUBLE-SEAL ASSEMBLY

(75) Inventors: Bradley R. Rightnour, State College, PA (US); Michael A. Goss, State College, PA (US); Paul H. Silvis, Port Matilda, PA (US); Christopher S. Cox, State College, PA (US)

(73) Assignee: Restek Corporation, Bellefonte, PA (US)

( * ) Notice: Subject to any disclaimer, the term of this patent is extended or adjusted under 35 U.S.C. 154(b) by 163 days.

(21) Appl. No.: 10/888,438

(22) Filed: Jul. 9, 2004

(65) Prior Publication Data

US 2005/0145110 A1    Jul. 7, 2005

Related U.S. Application Data

(63) Continuation-in-part of application No. 10/098,654, filed on Mar. 15, 2002, now abandoned.

(51) Int. Cl.
   *B01D 53/02*    (2006.01)
(52) U.S. Cl. ............ 95/89; 95/82; 96/105; 96/106; 73/23.42
(58) Field of Classification Search .......... 96/105, 96/101, 104, 106, 107; 73/23.35, 23.39, 73/23.41, 23.42; 95/82, 89; 210/656, 198.2
   See application file for complete search history.

(56) References Cited

U.S. PATENT DOCUMENTS

| | | | | |
|---|---|---|---|---|
| 4,026,803 A | * | 5/1977 | Abrahams et al. | 210/198.2 |
| 4,283,280 A | * | 8/1981 | Brownlee | 210/198.2 |
| 4,296,634 A | * | 10/1981 | Goodale et al. | 73/864.86 |
| 4,655,917 A | * | 4/1987 | Shackelford et al. | 210/198.2 |
| 5,338,448 A | * | 8/1994 | Gjerde | 210/198.2 |
| 5,423,982 A | * | 6/1995 | Jungbauer et al. | 210/198.2 |
| 6,361,687 B1 | * | 3/2002 | Ford et al. | 210/198.2 |
| 6,442,995 B1 | * | 9/2002 | van der Maas | 73/23.35 |
| 6,679,989 B2 | * | 1/2004 | Willis et al. | 210/198.2 |
| 2004/0054286 A1 | * | 3/2004 | Audain et al. | 600/449 |

* cited by examiner

*Primary Examiner*—Duane Smith
*Assistant Examiner*—Robert A Clemente
(74) *Attorney, Agent, or Firm*—John F. A. Earley, III; Frank J. Bonini, Jr.; Harding, Earley, Follmer & Frailey, P.C.

(57) ABSTRACT

An inlet seal assembly for sealing an injection port member in a chromatography instrument, comprising an injection port member having a raised metal ring, an inlet seal member with an upper surface, a peripheral groove formed in the inlet seal member upper surface, a soft resinous plastic material ring positioned in the peripheral groove opposite the raised metal sealing ring, a reducing nut holding the inlet seal member against the injection port member, and threads connecting the reducing nut to the injection port member whereby to press the soft ring against the raised metal sealing ring to form a seal. The inlet seal assembly also may have a bottom seal between the inlet seal member and the reducing nut. A method of making and using the inlet seal assembly.

16 Claims, 3 Drawing Sheets

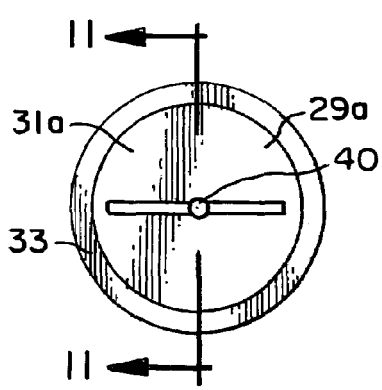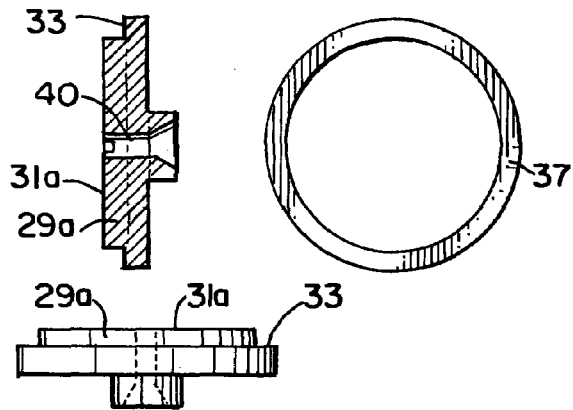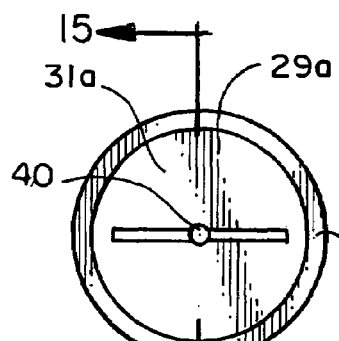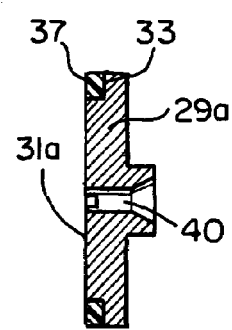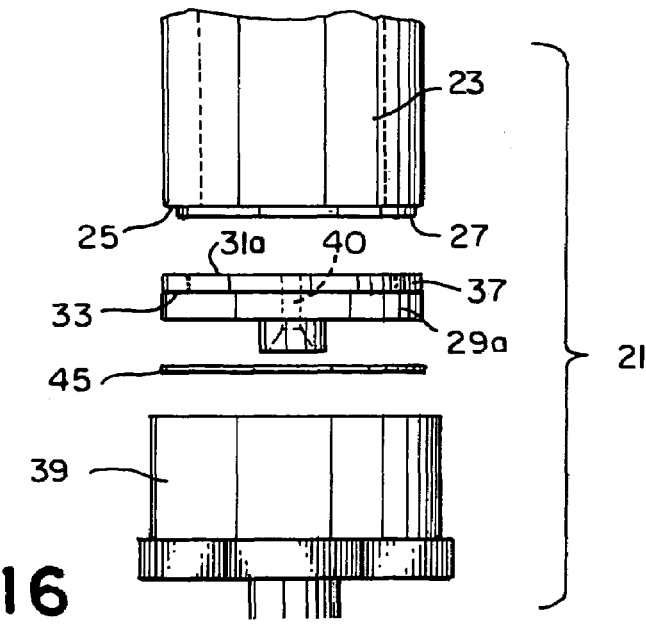

INLET DOUBLE-SEAL ASSEMBLY

CROSS REFERENCE TO RELATED APPLICATIONS

This patent application is a continuation-in-part of U.S. patent application Ser. No. 10/098,654, filed Mar. 15, 2002 now abandoned.

BACKGROUND OF THE INVENTION

1. Field of the Invention

This invention relates to chromatography, and more particularly concerns a new inlet seal assembly and method for use with gas chromatography instruments.

2. Description of the Prior Art

The prior art inlet seal member which is used to make a leak free seal between an injection port member of a split/splitless injector and a reducing nut is made from stainless steel and may be coated with some material, i.e., gold, silver, etc. The seal is made by placing an inlet seal member in a reducing nut which has female threads that thread into male threads on the outer surface of the injection port member. The bottom surface of the injection port member has a small raised circular sealing ring of metal, and the seal is made by tightening the reducing nut which holds the inlet seal member to cause the raised circular sealing ring on the injection port member to cut into the top surface of the inlet seal member and make a metal to metal seal.

This prior art arrangement has a number of problems. For example, excessive torque must be used to achieve a leak free seal between the top surface of the inlet seal member and the sealing ring. Also, the injection port member and the inlet seal member must be machined to tight tolerances to insure squareness on both the injection port circular sealing ring and the inlet seal member upper surface or the integrity of the seal is compromised.

Also, the injection port circular sealing ring may become scratched, dented, or otherwise damaged and this compromises the seal.

SUMMARY OF THE INVENTION

It is an object of the invention to overcome the disadvantages of the prior art and to provide a new inlet seal assembly to allow easier and more reliable sealing of the injection port member. The new inlet seal assembly incorporates a soft sealing surface ring on the upper and/or bottom surface of the inlet seal member to allow for easier compression of the metal sealing ring to the face of the inlet seal member. The new seal assembly incorporates a secondary machine surface, a soft peripheral ring on the upper surface of the inlet seal member, which allows for placement of a secondary material, such as Teflon, Graphite, Nickle, Silver, Copper, Viton, Lead, or Vespel, which is a trademark of E.I. Du Pont de Nemours Corporation, Wilmington, Del., and this compressible material is added to the inlet seal member at the circle where the seal occurs.

This new arrangement of the inlet seal assembly, which incorporates a soft material composition, such as Vespel, enables us to achieve a better and more reliable seal between the injection port metal sealing ring and the inlet seal member even though the metal sealing ring surface may have become dented, scratched, or otherwise damaged. The new inlet seal assembly also allows for sealing under minimal torque conditions.

BRIEF DESCRIPTION OF THE DRAWINGS

FIG. 9 is a view in top plan of the new inlet seal member;

FIG. 10 is a view in side elevation of the inlet seal member of FIG. 9 and shows the peripheral groove in the inlet seal member;

FIG. 11 is a view in section of the inlet seal member taken as indicated by the lines and arrows 11-11 of FIG. 9;

FIG. 12 is a view in top plan of the soft Vespel ring for the new inlet seal member;

FIG. 13 is a view in top plan of the new inlet seal member;

FIG. 14 is a view in side elevation of the new inlet seal member; and

FIG. 15 is a view in cross section of the new inlet seal member;

FIG. 16 is an exploded view in front elevation of an inlet sealing ring assembly of the invention;

DETAILED DESCRIPTION

Figure 1:
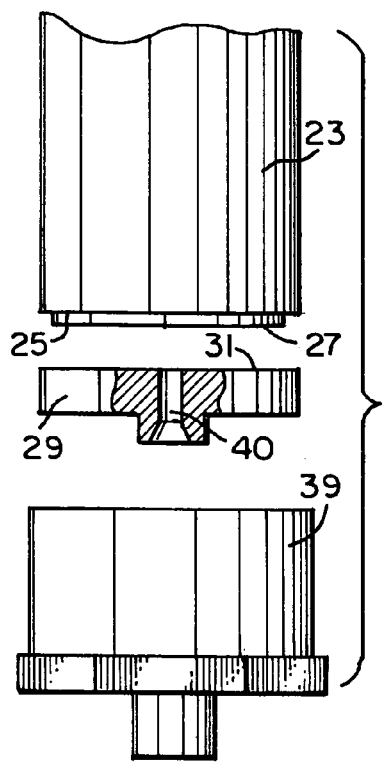
FIG. 1 is an exploded view in front elevation of an inlet sealing ring assembly of the prior art.
Figure 2:
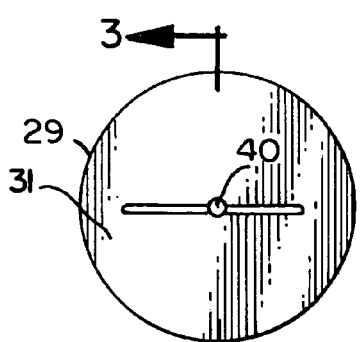
FIG. 2 is a view in top plan of the inlet seal member of FIG. 1.
Figure 3:
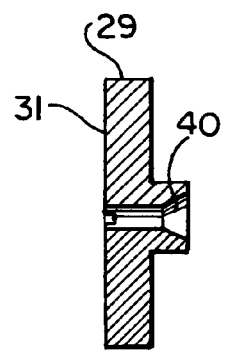
FIG. 3 is a view in section taken as shown by the arrows 3-3 in FIG. 2.
Figure 4:
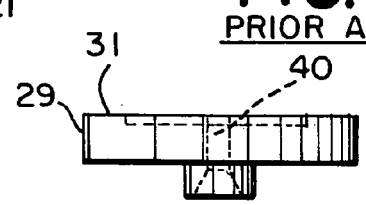
FIG. 4 is a view in side elevation of the inlet seal member of FIG. 3.
Figure 5:
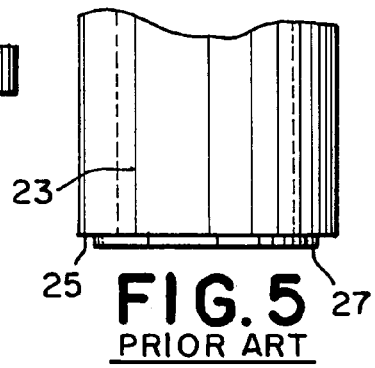
FIG. 5 is a view in side elevation of the injection port member.
Figure 6:
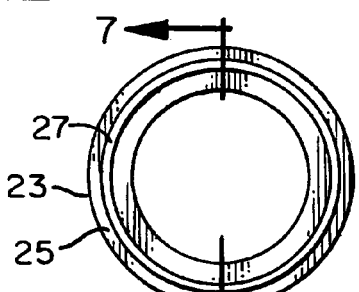
FIG. 6 is a view in bottom plan of the injection port member and shows the metal sealing ring.
Figure 7:
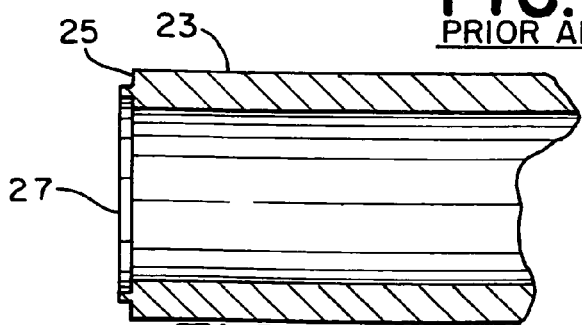
FIG. 7 is a view in section of the injection port member and shows the metal sealing ring.
Figure 8:
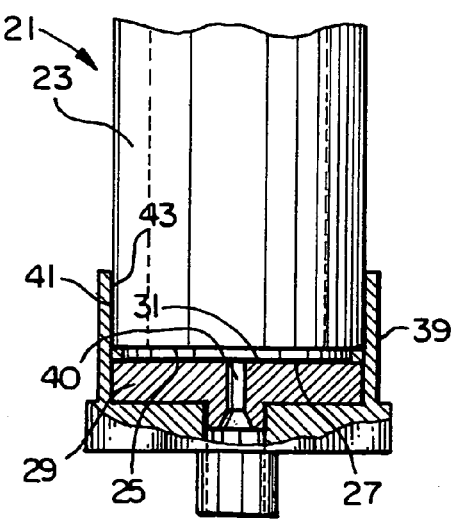
FIG. 8 is an assembled view of the prior art inlet seal assembly including the injection port member, the inlet seal member, and the reducing nut member which is screwed on to the injection port member.

Turning now to the drawings, there is shown in FIG. 1 a prior art inlet seal assembly 21 for sealing an injection port member 23 which includes injection port member 23 having a bottom surface 25 with a raised metal sealing ring 27. An inlet seal member 29 is provided with an upper surface 31 and the metal sealing ring 27 digs into the upper surface 31 to make a seal which may not be effective if the ring 27 or surface 31 is damaged.

The new inlet seal member 29a (FIG. 9-12) includes a peripheral groove 33 formed in the periphery of the inlet seal member 29a. A soft Vespel ring 37 is positioned in the peripheral groove 33 opposite the raised metal sealing ring 27 of injection port member 23. A reducing nut 39 forms a cup-like chamber which holds the inlet seal member 29a, and threads 41 and 43 connect the reducing nut 39 to the injection port member 23 whereby turning the reducing nut 39 which presses the soft vespel ring 37 of the inlet seal member 29a against the raised metal sealing ring 27 to form a seal between the inlet seal member 29a and the injection port member 23.

Figure 17:
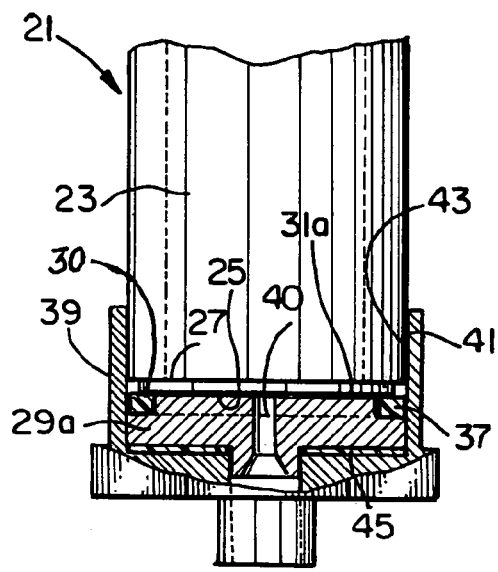
FIG. 17 is an assembled view of the inlet seal ring assembly.

In operation, the method of sealing an injection port member 23 in a gas chromatography machine is by providing an injection port member 23 having a bottom surface 25 with a raised metal sealing ring 27. An inlet seal member 29a is provided with an upper surface 31a, and a peripheral groove 33 is formed in the upper surface 31a of the inlet seal member 29a. The peripheral groove 33 is filled with a soft Vespel resinous material to form a soft Vespel resinous material ring 37. A seal 30 is formed between the injection port member 23 and the inlet seal member 29a by pressing the raised metal sealing ring 27 into the Vespel ring 37 by turning the reducing nut 39 on its threads. The seal is formed by tightening the threads between the reducing nut 39 and injection port member 23. A preferred embodiment of the invention is provided with a washer 45, as shown in FIGS. 16 and 17, between the inlet seal member 29a and the reducing nut 39.

When the inlet seal assembly is assembled, gas or liquid is ejected from the injection port member 23 through the opening 40 in the inlet seal member 29a and through the opening in reducing nut 39.

Ring 27 is preferably circular but it may assume other shapes, if desired. The word "ring" as used herein is meant to include those other shapes, such as square, or rectangular, etc. Also, the word "fluid" as used herein is meant to include liquid and/or gas.

Figure 20:
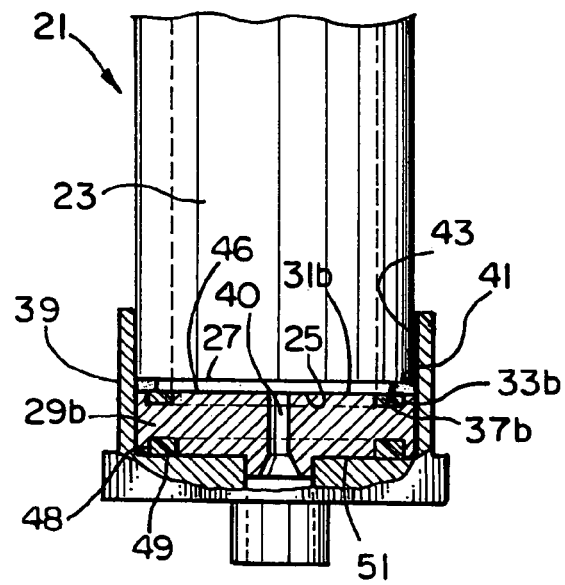
FIG. 20 is a view in cross section of another embodiment of the inlet sealing ring assembly of the invention.
Figure 18:
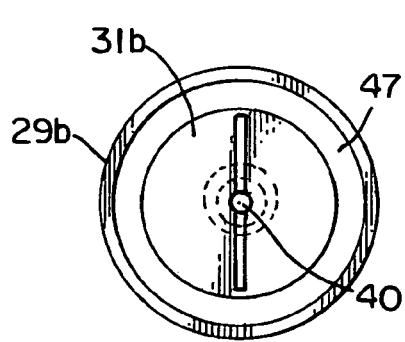
FIG. 18 is a view in top plan of another embodiment of inlet seal member.
Figure 19:
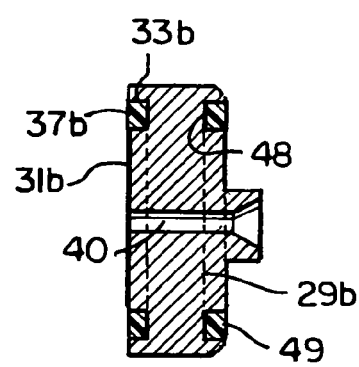
FIG. 19 is a view in section of the embodiment of inlet seal member shown in FIG. 18.

FIGS. 18 to 20 show another form of the invention, one that creates a double seal, a top seal 46 between the metal sealing ring 27 in the bottom surface 25 of the injection port member 23 and the upper surface 31b of the inlet seal member 29b. The upper surface 31b of inlet seal member 29b includes a circular groove 33b near the edge of the upper surface 31b of the inlet seal member 29b. Groove 33b is filled with Vespel synthetic resinous material to form a ring 37b which juts out from the groove 33b. In operation, the metal sealing ring 27 contacts the resinous ring 37b to depress the contact area of the ring 37b and form a seal 46.

Also the bottom surface of inlet seal member 29b is provided with a circular groove 48 which is filled with a Vespel ring 49 that extends out from groove 48 to be compressed against the bottom inside surface of the reducing nut 39 and form a bottom seal 51, thus providing a double seal 51 and 46.

This double seal version of the invention permits the elimination of washer 45 since it prevents the inlet seal number 29a from bending in the cup of the reducing nut 39.

The invention claimed is:

1. An inlet seal assembly for sealing an injection port member in a gas chromatography instrument, comprising
   an injection port member having a bottom surface with a raised metal ring,
   an inlet seal member with an upper surface,
   a peripheral groove formed in the upper surface of the inlet seal member,
   a soft ring made of resinous plastic material positioned in the peripheral groove of the inlet seal member opposite the raised metal sealing ring of the injection port member,
   a reducing nut holding the inlet seal member against the injection port member,
   thread means connecting the reducing nut to the injection port member, and
   a seal formed by the soft ring of the inlet seal member pressing against the raised metal ring of the injection port member when the reducing nut is tightened on to the injection port member via the thread means to cause the soft ring of the inlet seal member to press against the raised metal sealing ring of the injection port member.

2. The inlet seal assembly of claim 1, the injection port member being a hollow tube.

3. The inlet seal assembly of claim 1,
   wherein the reducing nut forms a cup-like chamber holding the inlet seal member and has threads along the inside of the sides of the cup which mesh with threads on the outer side surface of the injection port member.

4. The inlet seal assembly of claim 1,
   said inlet seal member having a bottom surface, and further including
   a bottom peripheral groove formed in the bottom surface of the inlet seal member,
   a bottom soft ring made of resinous plastic material positioned in the bottom groove of the inlet seal member,
   said bottom ring extending downwardly out of the bottom groove so as to touch the upper surface of the reducing nut to squeeze the bottom ring and make a bottom seal between the bottom of the inlet seal member and the upper surface of the reducing nut,
   thus forming a double seal of the inlet seal member comprising an upper seal and a bottom seal.

5. The inlet seal assembly of claim 4,
   the bottom soft ring being made of polytetrafluoroethylene, graphite, nickel, silver, copper, viton, lead, or a resinous plastic material.

6. The inlet seal assembly of claim 1,
   the soft ring being made of polytetrafluoroethylene, graphite, nickel, silver, copper, viton, lead, or a resinous plastic material.

7. A method of sealing an injection port member in a gas chromatography instrument comprising,
   providing an injection port member with a metal ring on its bottom surface,
   providing an inlet seal member having an upper surface,
   forming a peripheral groove on the upper surface of the inlet seal member,
   filling the peripheral groove with a soft resinous plastic material to form a ring,
   placing the inlet seal member in a reducing nut between the nut and the injection port member,
   connecting the reducing nut to the injection port member by providing threads between them,
   forming a seal by tightening the threads between the reducing nut and the injection port member to press the metal sealing ring onto the soft ring to form a seal between the injection port member and the inlet seal member.

8. The method of claim 7, including
   using the injection port assembly by ejecting gas or liquid from the injection port member through an opening in the inlet seal member and through an opening in the reducing nut.

9. An inlet seal assembly for sealing an injection port member in a gas chromatography instrument, comprising
   an injection port member having a bottom surface with a raised metal ring,
   an inlet seal member with an upper surface,
   a peripheral groove formed in the upper surface of the inlet seal member,
   a soft ring made of resinous plastic material positioned in the peripheral groove of the inlet seal member opposite the raised metal sealing ring of the injection port member, a reducing nut holding the inlet seal member against the injection port member, and thread means connecting the reducing nut to the injection port member whereby to press the soft ring of the inlet seal member against the raised metal sealing ring of the injection port member to form a seal between the sealing ring and the injection port member, said inlet seal member having a bottom surface, a bottom peripheral groove formed in the bottom surface of the inlet seal member, a bottom soft ring made of resinous plastic material positioned in the bottom groove of the inlet seal member, said bottom ring extending downwardly out of the bottom groove so as to touch the upper surface of the reducing nut to squeeze the bottom ring and make a bottom seal between the bottom of the inlet seal member and the upper surface of the reducing nut, thus forming a double seal of the inlet seal member comprising an upper seal and a bottom seal.

10. An inlet seal assembly for sealing an injection port member in a gas chromatography instrument, comprising an injection port member having a bottom end portion having a sealing surface, an inlet seal member with an upper surface, a groove formed in the upper surface of the inlet seal member, an upper soft ring positioned in the groove of the inlet seal member opposite the sealing surface of the injection port member, a reducing nut holding the inlet seal member against the injection port member, the reducing nut having a sealing surface, said inlet seal member having a bottom surface, a bottom groove formed in the bottom surface of the inlet seal member, a bottom soft ring positioned in the bottom groove of the inlet seal member, and thread means connecting the reducing nut to the injection port member and when tightened causing the upper soft ring of the inlet seal member to press against the sealing surface of the injection port member to form a seal between the sealing surface of the injection port member and the inlet seal member, said bottom soft ring extending downwardly out of the bottom groove so as to touch the sealing surface of the reducing nut to squeeze the bottom soft ring and make a bottom seal between the bottom surface of the inlet seal member and the sealing surface of the reducing nut when the thread means is tightened, thus forming a double seal of the inlet seal member comprising an upper seal and a bottom seal.

11. The inlet seal assembly of claim 10, the upper soft ring being made of polytetrafluoroethylene, graphite, nickel, silver, copper, viton, lead, or a resinous plastic material.

12. The inlet seal assembly of claim 10, the bottom soft ring being made of polytetrafluoroethylene, graphite, nickel, silver, copper, viton, lead, or a resinous plastic material.

13. The inlet seal assembly of claim 10, the injection port member being a hollow tube.

14. The inlet seal assembly of claim 10, wherein the reducing nut forms a cup-like chamber holding the inlet seal member and has threads along the inside of the sides of the cup which mesh with threads on the outer side surface of the injection port member.

15. A method of sealing an injection port member in a gas chromatography instrument comprising, providing an injection port member with an end portion having a sealing surface, providing an inlet seal member having an upper surface and a lower surface, forming a groove on the upper surface of the inlet seal member, filling the groove on the upper surface of the inlet seal member with an upper soft ring, forming a groove on the lower surface of the inlet seal member, filling the groove on the lower surface of the inlet seal member with a bottom soft ring, placing the inlet seal member in a reducing nut between the nut and the injection port member, connecting the reducing nut to the injection port member by providing threads between them, the reducing nut having a sealing surface, forming an upper seal by threading the reducing nut onto the injection port member causing the sealing surface of the injection port member to press onto the upper soft ring to form a the upper seal between the injection port member and the inlet seal member, and forming a bottom seal by threading the reducing nut onto the injection port member causing the sealing surface of the reducing nut to squeeze the bottom soft ring to form the bottom seal between the inlet seal member and the sealing surface of the reducing nut, thus forming a double seal of the inlet member comprising the upper seal and the bottom seal.

16. The method of claim 15, including using the injection port assembly by ejecting gas or liquid from the injection port member through an opening in the inlet seal member and through an opening in the reducing nut.

* * * * *